United States Patent [19]

Rabinovitz et al.

[11] Patent Number: 4,947,854
[45] Date of Patent: Aug. 14, 1990

[54] EPICARDIAL MULTIFUNCTIONAL PROBE

[75] Inventors: Raphael S. Rabinovitz; Craig J. Hartley; George P. Noon, all of Houston, Tex.

[73] Assignee: Baylor College of Medicine, Houston, Tex.

[21] Appl. No.: 243,915

[22] Filed: Sep. 13, 1988

[51] Int. Cl.$^5$ .............................................. A61B 8/12
[52] U.S. Cl. ............................ 128/662.04; 128/662.06
[58] Field of Search .................... 128/662.05–662.06, 128/661.08–661.1, 662.04

[56] References Cited

U.S. PATENT DOCUMENTS

| 3,124,132 | 3/1964  | Sullivan.              |
|-----------|---------|------------------------|
| 3,661,146 | 5/1972  | Peronneau ..... 128/2.05 F |
| 3,921,622 | 11/1975 | Cole ..................... 128/2 V |
| 3,955,560 | 5/1976  | Stein et al. ........... 128/21 E |
| 3,977,247 | 8/1976  | Hassler ................. 73/194 |
| 4,313,443 | 2/1982  | Lund .................... 128/642 |
| 4,355,643 | 10/1982 | Laughlin .............. 128/663 |
| 4,419,999 | 12/1983 | May et al. ............ 128/691 |
| 4,442,844 | 4/1984  | Navach ................. 128/663 |
| 4,541,433 | 9/1985  | Baudino ................ 128/668 |
| 4,744,368 | 5/1988  | Young et al. ......... 128/662.04 |
| 4,823,800 | 4/1989  | Compos ................ 128/661.08 |

FOREIGN PATENT DOCUMENTS

270733 6/1988 European Pat. Off. .
2585944 2/1987 France .
217689 4/1987 France .

OTHER PUBLICATIONS

Vogel, S. et al., "The Use of the Doppler UTS Flowmeter ...", Conf: Proc. of the 2d Europ. Cong. on UTS in Medicine, Hamburg, Germany (12–16 May, 1975), pp. 169–173.
Nealeigh, R. C. et al., "A Venous Pulse Doppler Catheter-Tip Flowmeter for Measuring Arterial Blood Velocity, Flow & Diameter in Deep Arteries", ISA Transactions, vol. 15, No. 1, pp. 84–87, 1976.
Matre et al., "Continuous Measurement of Aortic Blood Velocity, after Cardiac Surgery, by means of an Extractable Doppler Ultrasound Probe", J. Biomec Eng., vol. 4, 1985, pp. 84–88.
Hill et al., "Perioperative Assessment of Segmental Left Ventricular Function in Man", Arch. Surg., vol. 115, May 1985, pp. 609–614.
Hartley et al., "Intraoperative Assessment of Regional Myocardial Function in Man", Cardiovascular System Dynamics Soc., Oct. 1987, p. 13.
Keagy et al., "Constant Postoperative Monitoring of Cardiac Output after Correction of Congenital Heart Defects", J. Thorac Cardiovasc. Surg., 1987; 93; 658–664.
Svennevig et al., "Continuous Monitoring of Cardiac Output Postoperatively Using an Implantable Doppler Probe", Scand J. Cardiovasc Surg., 20: 145–149, 1986.
Payen et al., "Comparison of Perioperative and Postoperative Phasic Blood Flow in Aortocoronary Bypass Grafts by means of Pulsed Doppler Echocardiography with Implantable Microprobes", Coronary Artery Surgery, vol. 74 (Suppl. III), Nov. 1986, 111-61–111-67.
Zhu et al., "Validation of a Single Crystal for Measurement of Transmural and Epicardial Thickening", Am. J. Physiol. 25 (Heart Circ. Physiol. 20), H1045-55, 1986.
Hartley et al., "Doppler Measurement of Myocardial Thickening with a Single Epicardial Transducer", Am. J. Physiol., 245 (Heart Circ. Physiol. 14), H1066-72, 1983.
Hartley et al., "Doppler Measurement of Myocardial Thickening with a Single Epicardial Transducer", American Journal of Physiology (Heart Circ. Physiol. 14), vol. 245, 1983, pp. 1066–1072.
T. Nakamura et al., "Ultrasonic Flowmeter with Implantable Miniature Sensors", Medical and Biological Engineering and Computing, vol. 24, No. 3, May 1986, pp. 235–242.
Svennevig et al., "Continuous Monitoring of Cardiac Output Postoperatively Using an Implantable Doppler Probe", Scandinavian Journal of Thoracic and Cardiovascular Surgery, vol. 20, 1986, pp. 145–149.
Hill et al., "Perioperative Assessment of Segmental Left Ventricular Function in Man", Arch. Surg., vol. 115, 1980, pp. 609–614.

Primary Examiner—Francis Jaworski
Attorney, Agent, or Firm—Vaden, Eickenroht, Thompson & Boulware

[57] ABSTRACT

An epicardial multifunctional probe has been designed to measure blood flow velocity and muscle thickening with two sensors. The probe is implantable and remains inside the patient after surgery. The probe is removable through a small opening in the patient's chest.

6 Claims, 4 Drawing Sheets

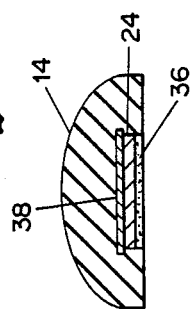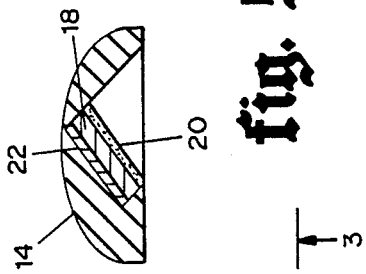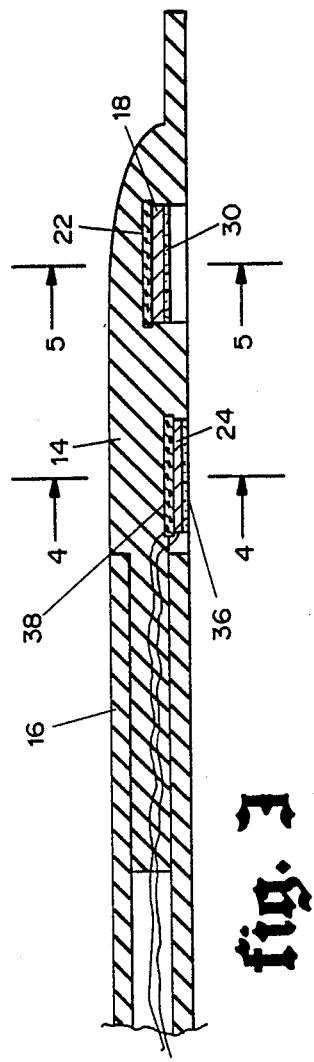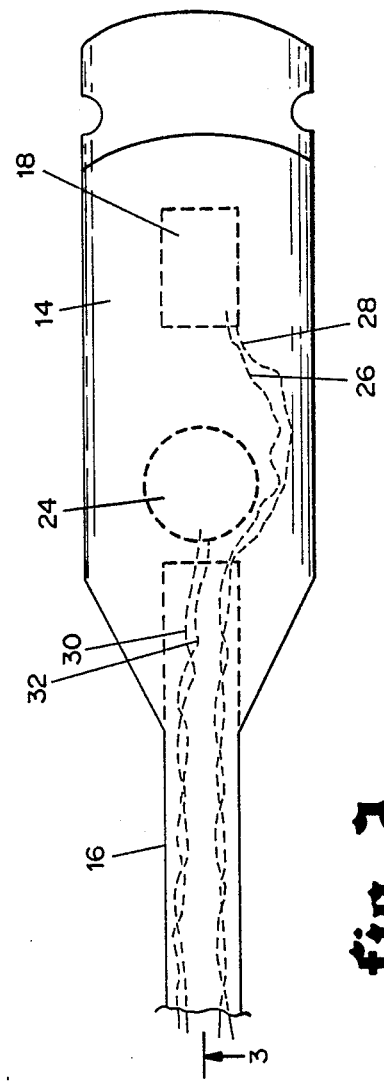

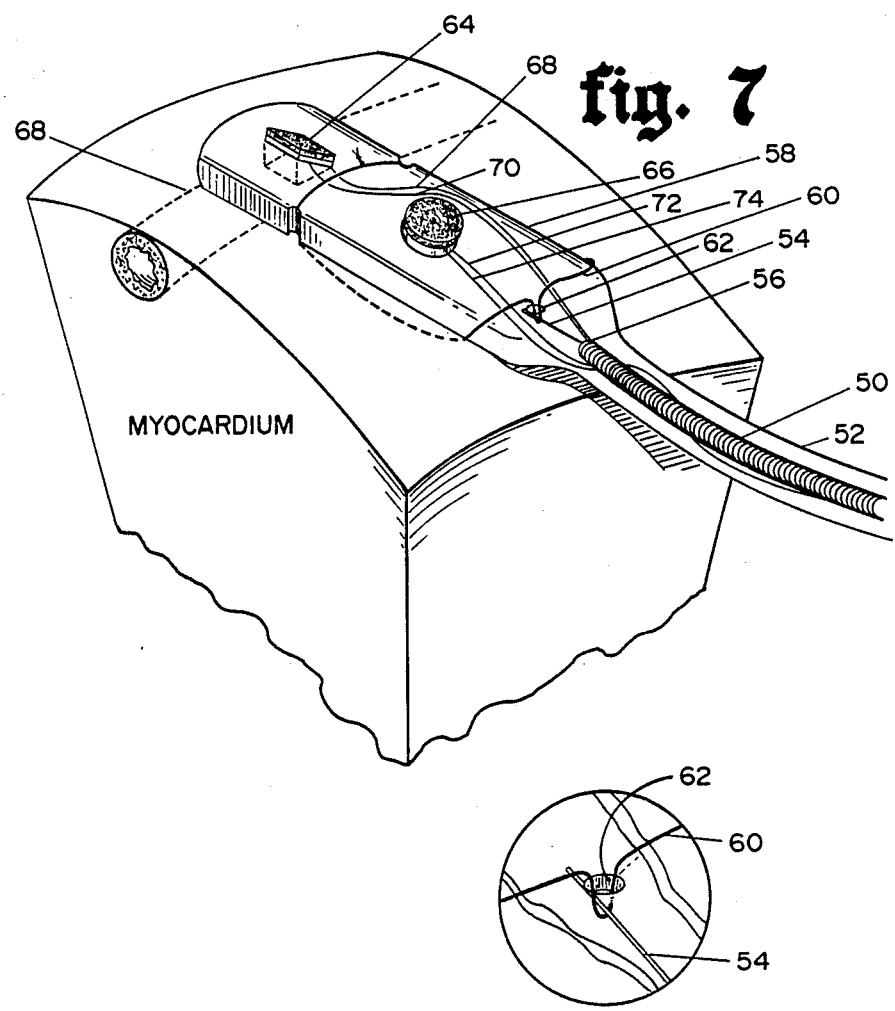

EPICARDIAL MULTIFUNCTIONAL PROBE

ORIGIN OF THE INVENTION

The invention described herein was made using federal funds and may be manufactured or used by or for the government of the United States of America for governmental purposes without payment of any royalties theron or therefor.

BACKGROUND AND SUMMARY OF THE INVENTION

Coronary artery bypass graft surgery is a typical procedure for treatment of chest pain or heart attack. During the operation veins are taken from another part of the body and used to bypass obstruction in the coronary arteries that surround the heart and supply blood to the heart muscle. Blood flow to the heart muscle is restored by use of the grafted vessels to areas where blood was reduced by obstructions in the coronary arteries. To keep the heart muscle functioning with a constant supply of blood, the bypass grafts must remain open.

If an inadequate supply of blood reaches the heart muscle, ischemia, or tissue death can occur. The heart muscles contract and relax during the blood pumping cycle. Upon contraction the heart muscle thickens and upon relaxation it thins. If the myocardial tissue (heart muscle tissue) is not supplied with sufficient blood and becomes ischemic, muscle contraction may be reduced or stop completely. The other healthy tissue around the ischemic tissue will continue to contract pulling and thinning the ischemic tissue. The thin ischemic tissue may bulge under pressure and an aneurysm can occur.

In monitoring the postoperative bypass patient attention should be directed not only to blood flow in the coronary arteries and the bypass graft, but also the function of the heart muscle supplied by the graft. The left ventricle of the heart pumps blood to the extremities of the body and to the coronary arteries which supply blood and are often the focus of bypass surgery. If there is ischemia in the myocardium of the left ventricle, the detection will indicate graft failure or drug evaluation. Early detection of ischemia is important in planning therapy to avoid irreversible damage and aneurysms.

Small biological sensors haven been developed which can be used to monitor responses during surgery. Some sensors are adapted for implantation in the patient and remain postoperative to constantly monitor function. Blood flow sensors have been developed including electromagnetic type flow meters and ultrasonic Doppler transducers consisting of a single piezoelectric crystal acting as an ultrasonic transmitter and receiver.

The implantable Doppler transducers used as blood flow velocity sensors are very small and can be used in a probe to monitor continuously the blood flow of vessels in a patient for a period of time, postoperative or otherwise. The sensor or probe must be secured to the vessel to assure proper flow velocity measurements. Examples of Doppler transducers used in flow probes and the technique has been reported by Payen, D. et al. "Comparison of Preoperative and Postoperative Phasic Blood Flow in Aortocoronory Venous Bypass Grafts by Means of Pulsed Doppler Echocardiograph with Implantable Microprobes; *Circ;* Vol. 74 (Suppl. III), pp. 61–67 (1986); Svenning, J. L. et al, "Continuous Monitoring of Cardiac Output Postoperatively Using an Implantable Doppler Probe, *Scand. J. Thor. Cardiovasc. Surg.*, Vol. 20, pp. 145–149 (1986); and Baudino, U.S. Pat. No. 4,541,433 issued Sept. 17, 1985.

Several methods have been described to provide measurement of regional myocardial function. Sensors are used to measure the thickening of the myocardial tissue. For continuous assessment of regional dimensions of the left ventricular wall, the distance was measured between a pair of ultrasonic sensors plunged into the myocardium to a depth of 7 mm from the epicardium, 10 mm apart. The myocardium is pierced twice. Hill, R. C. et al "Perioperative Assessment of Segmental Left Ventricular Function in Man," *Arch. Surg.*, Vol. 115, 609 (1980).

Myocardial thickening-sensors have been developed by our laboratories which are attached to the epicardial (outer) surface of the heart muscle. Only one sensor is needed and invasion into the myocardium is not necessary for use. The sensors are small piezoelectric crystals which detect thickening of the myocardium as more fully discussed in the cited references. Hartley, C. J. et al, "Intraoperative Assessment of Regional Myocardial Function in Man," Proc. 8th Int'l. Conf. of the Cardiovasc. System Dynamics Soc'y., Osaka, Japan, Vol. 9 (1–3) pp. 13 (1987); Zhu, W. X. et al., "Validation of a single crystal for the measurement of transmural and epicardial thickening", *Am. J. Physiol.*, Vol. 251, pp. H1045–H1055 (1986); Hartley et al., "Doppler measurement of myocardial thickening with a single transducer", *Am. J. Physiol.*, Vol. 245 (*Heart Circ. Physiol.* 14), pp. H1066–H1072 (1983).

The present invention is a multifunctional probe with one sensor to measure blood flow in the coronary artery and another sensor to measure myocardial thickening. The probe containing both sensors is implantable and useful for intra and postoperative monitoring. The small probe can be removed from the closed patient several days after surgery through a small opening in the patient's chest. The removal of the probe requires no invasive surgery. During the monitoring process the lead wires extend through this small opening. When the probe is no longer needed gently traction is placed on the tube and lead wires and the probe is removed.

The sensors are contained in a probe body of biocompatible material such as silicon rubber which is nonreactive to body tissues and fluids. The placement of the sensors in the probe body can be in any configuration and spacing desired. For use in postoperative monitoring of both coronary artery blood flow and ventricular thickening, the spacing would typically include a crystal placed over an epicardial coronary artery to measure blood flow velocity spaced about 4 mm to about 8 mm from a crystal which measures regional myocardial function.

The probe body with a blood flow velocity sensor and a myocardial thickening sensor is lightly sutured less than 2 mm to the outer surface of the epicardium. The blood flow velocity sensor is positioned over the coronary artery without any need for dissection of the artery or the adjacent tissue. The thickening sensor generally is placed over the myocardium which is supplied with the blood from the coronary artery and the bypass graft to measure the thickening of the heart muscle. The probe body terminates in a flexible tube through which the lead wires extend. The tube extends outside the patient's body similar to a surgical drainage tube and the lead wires are connected to the electronic monitoring equipment.

BRIEF DESCRIPTION OF THE DRAWINGS

FIG. 2 is a top view of the probe with the sensors in phantom.

FIG. 3 is a length wise section of the probe take at lines 3—3 of FIG. 2.

FIG. 4 is a cross-section through line 4—4 of FIG. 3.

FIG. 5 is a cross-section through line 5—5 of FIG. 3.

FIG. 7 is an alternative embodiment of the probe in perspective view sutured in place over a coronary artery and myocardium.

FIG. 8 is an enlarged view of the suture attachment of the alternative embodiment.

DETAILED DESCRIPTION OF THE INVENTION

Figure 1:
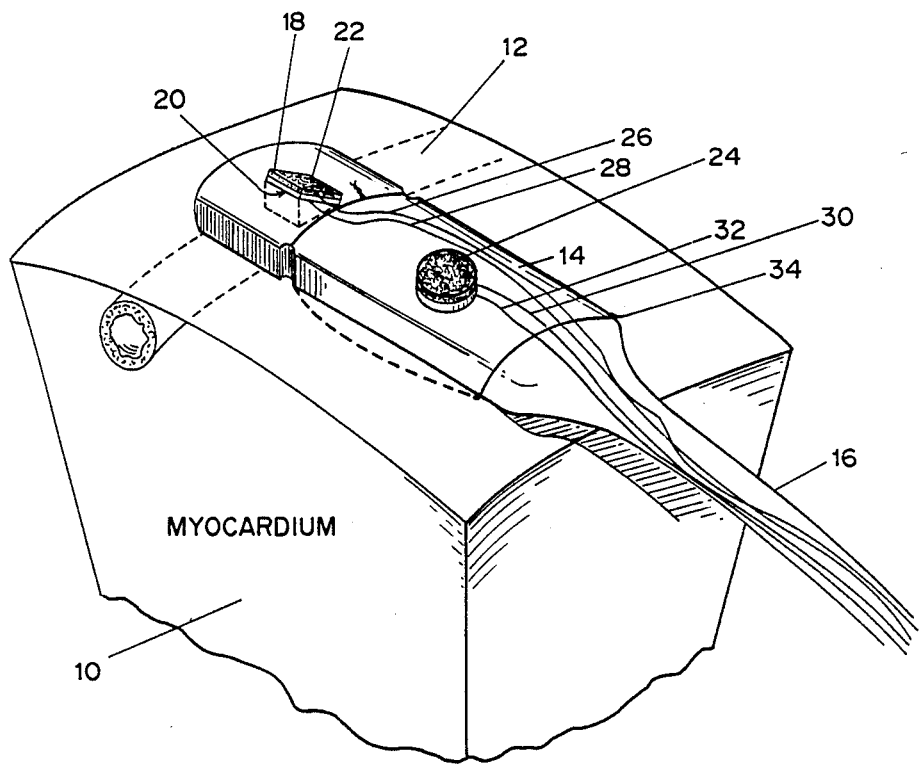
FIG. 1 is an enlarged perspective view in partial transparency of the installed probe on a coronary artery and myocardial tissue.

FIG. 1 is a view of the installed probe with a portion of the myocardium 10 shown with an artery 12. The coronary arteries supplying blood to the heart are often embedded and surrounded to a great degree with heart muscle. The probe body 14 is a generally rectangular piece of biocompatible, nonbioreactive material such as silicon rubber. The probe body is sized to be placed in a human heart and typical dimensions are 5 mm to 7 mm in width and 14 mm to 20 mm in length, although any size desired can be used to practice the invention which is capable of implantation in the body.

The probe body terminates in a flexible tube 16 which extends outside the patient's body. A generally flat piezoelectric crystal 18 is partially embedded in probe body 14 at an angle of about 30° to 60° sideways to the surface of the probe body which faces the vessel after attachment. This crystal 18 is the blood flow velocity sensor. The crystal is typically 10 MHz or 20 MHz but generally any frequency between 5 and 20 MHz can be used. One face of the crystal 18 has a thin coating of epoxy 20 for protection. This face of the crystal is adjacent to the coronary artery to be monitored. One the other face of the crystal 18 is a layer 22 of acoustic material such as cork for sound absorbing. A pair of lead wires 26 and 28 are soldered one to each face of crystal 18. The lead wires extend through the probe body into and through flexible tube 16.

In FIG. 1 the thickening sensor is a generally flat piezoelectric crystal 24 spaced from crystal 18 which measures blood flow velocity. The thickening sensor 24 is placed over the myocardium region to be monitored for muscle thickening. The thickening sensor is generally in close proximity to the coronary artery furnishing blood to the myocardial tissue monitored. The crystal used as the thickening sensor is partially embedded in the probe body 14 such that one face is flush with the outer surface of the probe body. The thickening sensor is typically a 10 MHz or 20 MHz crystal, however any frequency in the 5 MHz to 20 MHz each face of crystal 24 and extend through flexible tube 16. The lead wires are connected to the electronic display units outside the patients body.

The probe body 14 is sutured through the epicardium with suture 34 looping over the probe body and slightly penetrating the surface about 2 mm. The blood flow velocity sensor 18 is placed over the coronary artery 12 to monitor blood flow velocity. The thickening sensor 24 is placed over the myocardium to measure thickening.

FIG. 2 is a top view of the probe body 14 showing the blood flow velocity sensor 18 and the thickening sensor 24 and their respective lead wires 26 and 28; and 30 and 32 extending through tube 16.

FIG. 3 shows thickening sensor 24 with one face flush with the outer surface of probe body 14 which is placed over the myocardium to be monitored. The outer face of sensor 24 is coated with a layer of epoxy 36. The other face has an acoustical backing layer 38 such as cork. The blood flow velocity sensor 18 is shown in FIG. 3 with the epoxy layer or coating 20 and acoustical layer 22. The blood flow velocity sensor is at an angle, as described earlier, facing the coronary artery.

FIG. 4 is a cross-section through the probe, showing the flush alignment of the epoxy coated surface 36 of the thickening sensor 24 with the surface of probe body 14. The probe body surrounds the rest of thickening sensor 24 with acoustical layer 38 so that thickening sensor 24 is partially embedded in the probe body 14. FIG. 5 is a cross-section through the probe body 14 at the angle of blood flow velocity sensor 18. The epoxy coated face 20 of the sensor 18 is exposed to the adjacent coronary artery (not shown). The rest of the blood flow velocity probe is essentially embedded by the probe body 14.

Figure 6:
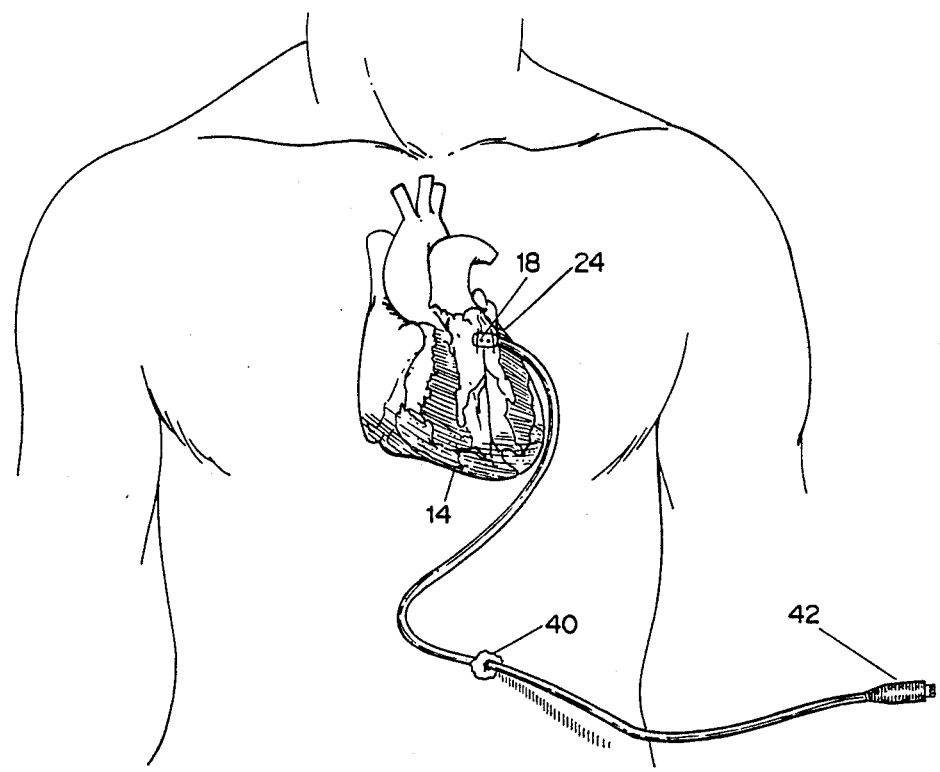
FIG. 6 is a view of the probe as positioned in the human body after surgery.

FIG. 6 is a view of a human body with the probe 14 sutured into place and flexible tube 16, containing the lead wires, extending through a small incision in the chest wall. The terminal end 42 of the lead wires are connected to the electronic devices which read the signals from the sensors 18 and 24. The probe 14 is small enough to be removed through incision 40 without surgery by gentle traction on the tube 16 and the lead wires.

An alternative embodiment of the sensor probe is provided with a suturing release feature shown in FIG. 7. The probe can be secured to the epicardium by the surgeon with tension as desired. The release feature allows a slackening of the suture when the probe is removed.

A flexible cable 50 extends through the central opening of flexible tube 52. The flexible cable 50 as shown in FIG. 7 is made of a central wire 54 wrapped with a tight coil 56. The flexible tube 52 extends outside the patient's body with the cable 50 inside the tube's central opening. The cable 50 will retract inside the tube upon traction on the end of the cable which extends outside the patient's body.

The cable 50 as shown in FIG. 7 has the terminal portion of wire 54 extending in the probe body 58. The central opening of flexible tube 52 communicates with an opening in the probe body adjacent to the tube's attachment to the probe body 58. The wire 54 not wrapped by coil 56 extends into a small opening in the probe body 58. A suture 60 is looped around the wire 54 near its terminal end in the probe body. The two ends of the suture 60 extend through an opening 62 in the probe adjacent to the portion of wire 54 of cable 50 which has the suture 60 looped in place.

FIG. 8 is an enlarged view of the wire 54 which has the suture 60 looped over wire 54. The ends of suture 60 extend through opening 62 in the probe body so that the suture ends emerge from the top of the probe body.

The other components of the sensor probe are as described earlier. A blood flow velocity sensor 64 and thickening sensor 66 are contained in the probe body 58. The lead wires 68 and 70 extending from sensor 64 and lead wires 72 and 74 extending from sensor 66 extend through the probe body into flexible tube 52 to ultimately connect with the patient's monitoring equipment.

The multifunctional probe shown in FIG. 8 is positioned so that the blood flow velocity sensor 64 is placed over the coronary artery 68 and the thickening sensor 66 is over the myocardium. The two ends of suture 60 which extend from opening 62 on top of probe body 58 are inserted into the myocardium very lightly at about 2 mm or less on either side of the probe body. The ends are brought up on top of the probe body and tied off as shown with knot 70 thus securing the multifunctional sensor probe in place on the epicardium.

In FIG. 7 there are slight indentations 72 and 74 on either side of the probe body where the suture 60 is drawn up. FIG. 7 shows the alternative embodiment sutured into place.

The removal of the probe body 58 is faciliated by the cable 50. When the probe is to be removed, the end of cable 50 which extends outside the patient's body is pulled with gentle traction. The wire 54 retracts inside the probe body and tube 52 to release the looped suture 60 from inside the probe body 58. The retraction of wire 54 of cable 50 provides a slackened amount of suture around the probe body 58. The probe itself is then removed by traction on the flexible tube 52. The cable 50 can be made of any flexible length of cable material in addition to coil wrapped wire as shown in FIGS. 7 and 8.

What is claimed is:

1. A multifunctional biological sensorprobe comprising:
   a probe body of a biocompatible, nonbioreactive material;
   a first piezoelectric crystal that both receives and transmits signals partially embedded in said probe body with one exposed face at an angle between about 30° and about 60° at the outer surface of said probe body for measuring blood flow velocity in a vessel;
   lead wires extending from said first piezoelectric crystal;
   a second piezoelectric crystal that both receives and transmits signals partially embedded in said probe body with one face in a flush manner to the outer surface of said probe body for measuring muscle thickening; and
   lead wires extending from second piezoelectric said crystal.

2. A multifunctional biological sensor probe of claim 1 wherein:
   said probe body is a generally rectangular shaped flexible material.

3. A multifunctional biological sensor probe of claim 1 wherein:
   said probe body terminates in a flexible tube through which extend said lead wires from said first crystal and said second crystal.

4. A multifunctional biological sensor probe to claim 1 wherein:
   said first crystal and said second crystal are spaced apart from each other in the probe body so that said first crystal is adapted to position over the coronary artery and said second crystal is adapted to position over the myocardium of a heart.

5. A multifunctional biological sensor probe of claim 1 wherein:
   said probe body terminates in a flexible tube;
   a flexible cable extending through the center portion of said flexible tube;
   said cable capable of retraction by remote actuation; and
   a suture looped around the cable in the flexible tube with said suture extending outside the flexible tube through an opening in the flexible tube.

6. A multivunctional biological sensor probe of claim 1 wherein:
   said probe body terminates in a flexible tube;
   a flexible cable extending through the center portion of said flexible tube and at least partially into an opening inside the probe body which opening communicates with the central opening of the flexible tube;
   said cable capable of retraction by remote actuation; and
   a suture looped around the cable in the flexible tube with said suture outside the probe body extending through an opening in the probe body.

* * * * *